(12) United States Patent
Hötten et al.

(10) Patent No.: US 6,972,321 B1
(45) Date of Patent: Dec. 6, 2005

(54) MONOMERIC PROTEIN OF THE TGF-β FAMILY

(75) Inventors: Gertrud Hötten, Herne (DE); Rolf Bechtold, Heidelberg (DE); Jens Pohl, Hambrücken (DE)

(73) Assignee: HyGene AG, Neuhausen am Rheinfall (CH)

( * ) Notice: Subject to any disclaimer, the term of this patent is extended or adjusted under 35 U.S.C. 154(b) by 234 days.

(21) Appl. No.: 10/048,458

(22) PCT Filed: Aug. 4, 2000

(86) PCT No.: PCT/EP00/07600

§ 371 (c)(1),
(2), (4) Date: Feb. 6, 2002

(87) PCT Pub. No.: WO01/11041

PCT Pub. Date: Aug. 4, 2000

(30) Foreign Application Priority Data

Aug. 6, 1999 (EP) .................................. 99115613

(51) Int. Cl.[7] .................. C07K 14/00; C12P 21/06; A61K 38/00
(52) U.S. Cl. .................... 530/350; 435/69.1; 514/2
(58) Field of Search ............... 530/350; 435/69.1; 514/2

(56) References Cited

U.S. PATENT DOCUMENTS 5,801,014 A * 9/1998 Lee et al. ................ 435/69.1

FOREIGN PATENT DOCUMENTS

| EP | 0915168 A | 5/1999 |
|----|-----------|--------|
| WO | WO 94 17099 A | 8/1994 |
| WO | WO 95 04819 A | 2/1995 |
| WO | WO 95 16035 A | 6/1995 |
| WO | WO 96 01316 A | 1/1996 |
| WO | WO 97 03188 A | 5/1999 |

OTHER PUBLICATIONS

Hüsken-Hind et al. J. Biol. Chem. 1994, vol. 269, pp. 19380-19384.*
Wolfman, N. et al. J. Clin Invest. 1997, vol. 100, pp. 321-330.*
Hüsken-Hindi, Pertra et al.: Journal of Biological Chemistry, (1994) vol. 269 No. 30 pp. 19380-19384, Jul. 24, 1994.
Amatayakul-Chantler, Supavadee et al.Journal of Biological Chemistry (1994) vol. 269, No. 44, pp. 27687-27691, Nov. 4, 1994.
Brunner, Amy M. et al.; Molecular Endocrinilogy, (1992) vol. 6, No. 10, pp. 1691-1700.
Brunner A. M. et al.; J Biol. Chem., (1989) 264 (23) pp 13660-13664.
Daopin S. et al. Science, US, American Association for the Advancement of Science, vol. 257, pp. 369-373.
M. P. Schlunegger et al. Nature, GB, MacMillan Journals Ltd, London, vol. 358, No. 358 p. 430-434-434.

* cited by examiner

*Primary Examiner*—Janet Andres
(74) *Attorney, Agent, or Firm*—Rothwell, Figg, Ernst & Manbeck

(57) ABSTRACT

The present invention is concerned with proteins selected from the members of the TGF-β superfamily, which are monomeric due to substitution or deletion of a cystein which is responsible for dimer formation. The invention is also concerned with nucleic acids, encoding such monomeric proteins, vectors or host cells containing the nucleic acids as well as with pharmaceutical compositions comprising the proteins or nucleic acids encoding the proteins. The pharmaceutical compositions can be applied advantageously for all indications for which the respective dimeric proteins are useful.

15 Claims, 2 Drawing Sheets

Name: <u>MP52, dimeric form</u>

Figure 1:
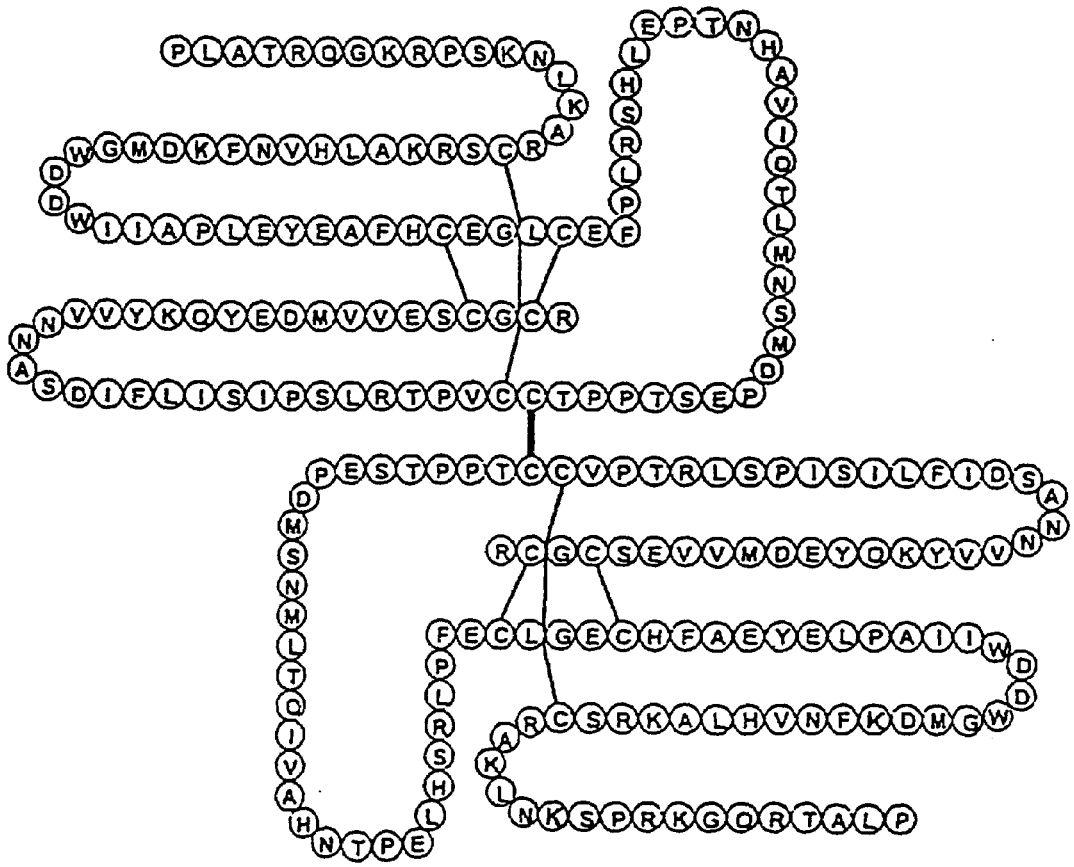
Figure 1:
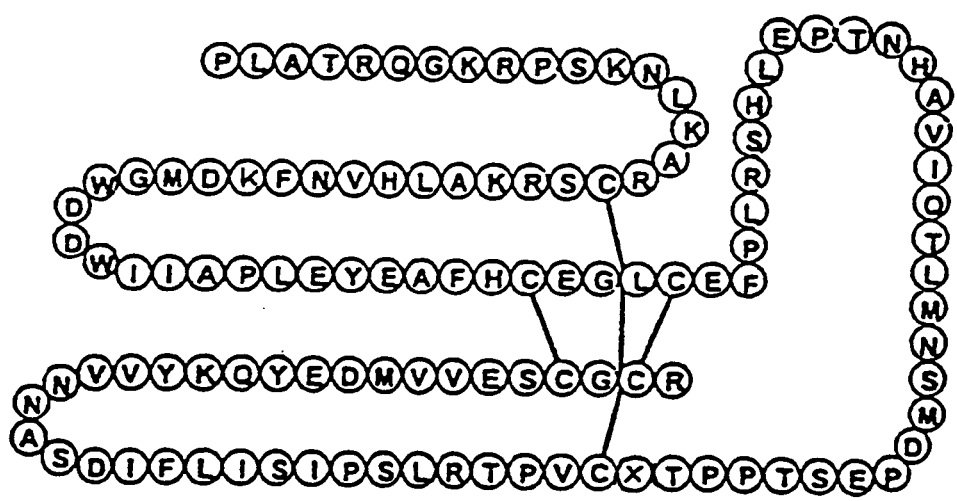

| | |
|---|---|
| Formula | $C_{1184}H_{1844}N_{330}O_{350}S_{22}$ |
| Molecular weight | 26994 Dalton |
| Amino acid composition | 238 amino acids |
| Disulfide bond | 7 bonds |

Primary structure

MONOMERIC PROTEIN OF THE TGF-β FAMILY

DESCRIPTION

The present invention concerns a biologically active protein from the TGF-β superfamily, wherein this protein remains in monomeric form due to substitution or deletion of a cysteine which is reponsible for the dimerization in the wild-type protein. Further the invention concerns a nucleic acid, which codes for a protein according to the invention, an expression vector containing such nucleic acid and a host cell, containing a corresponding nucleic acid or an expression vector, said nucleic acid being suitable for the expression of the protein. The invention also concerns a pharmaceutical composition containing the protein according to the invention or a nucleic acid coding therefor. The use of the pharmaceutical composition according to the invention concerns the prevention or treatment of all conditions which can also be treated with the dimeric form of the corresponding protein.

Many growth factors from the TGF-β superfamily (Kingsley, Genes and Development 8, 133–146 (1994) as well as the references cited therein) are relevant for a wide range of medical treatment methods and applications which in particular concern promotion of cell proliferation and tissue formation, including wound healing and tissue reproduction. Such growth factors in particular comprise members of the TGF-β (transforming growth factor, cf. e.g. Roberts and Sporn, Handbook of Experimental Pharmacology 95 (1990), page 419–472, editors: Sporn and Roberts), the DVR-group (Hötten et al., Biochem. Biophys. Res. Comm. 206 (1995), page 608–613 and further literature cited therein) including BMPs (bone morphogenetic protein, cf. e.g. Rosen and Thies, Growth Factors in Perinatal Development (1993), page 39–58, editors: Tsang, Lemons and Balistreri) and GDFs (growth differentiation factors), the inhibin/activin (cf. e.g. Vale et al., The Physiology of Reproduction, second edition (1994), page 1861–1878, editors: Knobil and Neill) and the GDNF protein family (Rosenthal, Neuron 22 (1999), page 201–203; Airaksinen et al. Mol Cell Neurosci 13 (1999), page 313–325). Although the members of the TGF-β superfamily show high amino acid homologies in the mature part of the protein, in particular 7 conserved cysteines, they show considerable variations in their exact functions. Often individual growth factors of these families exhibit a plurality of functions at the same time, so that their application is of interest in various medical indications. Some of these multifunctional proteins also have survival promoting effects on neurons in addition to functions such as e.g. regulation of the proliferation and differention in many cell types (Roberts and Sporn, supra; Sakurai et al., J. Biol. Chem. 269 (1994), page 14118–14122). Thus e.g. trophic effects on embryonic motoric and sensory neurons were demonstrated for TGF-β in vitro (Martinou et al., Devl. Brain Res. 52, page 175–181 (1990) and Chalazonitis et al., Dev. Biol. 152, page 121–132 (1992)). In addition, effects promoting survival are shown for dopaminergic neurons of the mid-brain for the proteins TGF-β-1, -2, -3, activin A and GDNF (glial cell line-derived neurotrophic factor), a protein which has structural similarities to TGF-β superfamily members, these effects being not mediated via astrocytes (Krieglstein et al., EMBO J. 14, page 736–742 (1995)).

Interesting members of the TGF-β superfamily or active variants thereof comprise the TGF-β proteins like TGF-β1, TGF-β2, TGF-β3, TGF-β4, TGF-β5 (U.S. Pat. No. 5,284,763; EP 0376785; U.S. Pat. No. 4,886,747; DNA 7 (1988), page 1–8), EMBO J. 7 (1988), page 3737–3743), Mol. Endo. 2 (1988), page 1186–1195), J. Biol. Chem. 265 (1990), page 1089–1093), OP1, OP2 and OP3 proteins (U.S. Pat. No. 5,011,691, U.S. Pat. No. 5,652,337, WO 91/05802) as well as BMP2, BMP3, BMP4 (WO 88/00205, U.S. Pat. No. 5,013,649 and WO 89/10409, Science 242 (1988), page 1528–1534), BMP5, BMP6 and BMP-7 (OP1) (Proc. Natl. Acad. Sci. 87 (1990), page 9841–9847, WO 90/11366), BMP8 (OP2) (WO 91/18098), BMP9 (WO 93/00432), BMP10 (WO 94/26893), BMP11 (WO 94/26892), BMP12 (WO 98/16035), BMP13 (WO 95/16035), BMP15 (WO 96/36710), BMP16 (WO 98/12322), BMP3b (Biochem. Biophys. Res. Comm. 219 (1996), page 656–662), GDF1 (WO 92/00382 and Proc. Natl. Acad. Sci. 88 (1991), page 4250–4254), GDF8 (WO 94/21681), GDF10 (WO95/10539), GDF11 (WO 96/01845), GDF5 (CDMP1, MP52) (WO 95/04819; WO96/01316; WO 94/15949, WO 96/14335 and WO 93/16099 and Nature 368 (1994), page 639–643), GDF6 (CDMP2, BMP13) (WO 95/01801, WO 96/14335 and WO95/16035), GDF7 (CDMP3, BMP12) (WO 95/01802 and WO 95/10635), GDF14 (WO 97/36926), GFD15 (WO 99/06445), GDF16 (WO 99/06556), 60A (Proc. Natl. Acad. Sci. 88 (1991), page 9214–9218), DPP (Nature 325 (1987), page 81–84), Vgr-1 (Proc. Natl. Acad. Sci. 86 (1989), page 4554–4558) Vg-1, (Cell 51 (1987), page 861–867), dorsalin (Cell 73 (1993), page 687–702), MIS (Cell 45 (1986), page 685–698), pCL13 (WO 97/00958), BIP (WO 94/01557), inhibin a, activin βA and activin βB (EP 0222491), activin βC (MP121) (WO 96/01316), activin βE and GDF12 (WO 96/02559 and WO 98/22492), activin βD (Biochem. Biophys. Res. Comm. 210 (1995), page 581–588), GDNF (Science 260 (1993), page 1130–1132, WO 93/06116), Neurturin (Nature 384 (1996), page 467–470), Persephin (Neuron 20 (1998), page 245–253, WO 97/33911), Artemin (Neuron 21 (1998), page 1291–1302), Mic-1 (Proc. Natl. Acad. Sci USA 94 (1997), page 11514–11519), Univin (Dev. Biol. 166 (1994), page 149–158), ADMP (Development 121 (1995), page 4293–4301), Nodal (Nature 361 (1993), page 543–547), Screw (Genes Dev. 8 (1994), page 2588–2601). Other useful proteins include biologically active biosynthetic constructs including biosynthetic proteins designed using sequences from two or more known morphogenetic proteins. Examples of biosynthetic constructs are disclosed in U.S. Pat. No. 5,011,691 (e.g. COP-1, COP-3, COP-4, COP-5, COP-7 and COP-16). The disclosure of the cited publications including patents or patent applications are incorporated herein by reference.

The occurence of proteins of the TGF-βsuperfamily in various tissuous stages and development stages corresponds with differences with regard to their exact functions as well as target sites, life span, requirements for auxiliary factors, necessary cellular physiological environment and/or resistance to degradation.

The proteins of the TGF-β superfamily exist as homodimers or heterodimers having a single disulfide bond. This disulfide bond is mediated by a specific and in most of the proteins conserved cysteine residue of the respective monomers. Up to now it was considered as indispensible for the biological activity that the protein is present in its dimeric form. Several publications indicated that biological activity can only be obtained for dimeric proteins and it was speculated that this dimer formation is important for further polymer formation of two or more dimers to achieve intercellular signal transmission by simultaneous binding to type I and type II receptors for the TGF-β superfamily proteins on cells. It was assumed that only this simultaneous binding to both kinds of receptors would allow for effective intercellular signal transmission for the benefit of the patient (Bone, volume 19 (1996), page 569–574).

A disadvantage of the use of these proteins as medicaments and their production is, that they are not readily obtainable in biologically active and sufficiently pure form by recombinant expression in prokaryots without intensive renaturation procedures.

Thus it was the object of the present invention to provide a simple and inexpensive possibility to reproducibly produce proteins exhibiting high biological activity, wherein this biological activity should essentially correspond to that of the dimers of the proteins of said families.

This object is solved according to the invention by a protein selected from the members of the TGF-β protein superfamily, such protein being necessarily monomeric due to substitution or deletion of a cysteine which is responsible for dimeric formation.

Surprisingly it has been found that the substitution or deletion of the cysteine, which normally effects the dimerization in the proteins, results upon expression and correct folding (proper formation of the intramolecular disulfide bridges) in a monomeric protein that retains the biological activity of the dimeric form. Even more surprisingly, it was found that at least some of the monomeric proteins show a higher activity, based on the weight of protein, than their respective dimeric forms. Apart from this improved biological activity an important advantage for the proteins according to the invention is that they can be expressed in a large amount in prokaryotic hosts and upon simple refolding of the monomers they are obtained in high purity and very high yield without the need to separate dimerized from non-dimerized (monomeric) protein. The findings of the present invention are very surprising since, as already mentioned above, it was common understanding that only a dimer of the morphogenetic proteins has biological activity. Despite this understanding the proteins according to the invention show an up to two-fold higher activity than that of the dimer on the basis of protein weight. The smaller size of the proteins of the invention, while maintaining the biological activity, can also be considered as advantageous, e.g. for applications concerning the brain since the monomeric protein can much easier pass the blood-brain-barrier than the dimeric form.

The proteins according to the invention encompass all proteins of the mentioned protein families that are normally present in dimeric form. Also parts of such proteins that retain substantial activity or fusion proteins or precursor forms of proteins shall be considered as encompassed by the present invention as well as biologically active naturally occurring or biosynthetic variants of TGF-β superfamily proteins, as long as they show at least considerable biological activity.

In a preferred embodiment of the present invention the monomeric protein is a mature protein or a biologically active part or variant thereof. The term "biologically active part or variant thereof" is meant to define either fragments retaining activity, precursor proteins that are e.g. cleaved at the site of activity to the mature form or show biological activity themselves, or also variants that still maintain essentially the biological activity of the wild-type protein. Such variants preferably contain conservative amino acid substitutions, but especially at the N-terminal part of the mature proteins even considerable deletions or substitutions do not lead to a considerable loss of biological activity. It is well within the skill of the man in the art to determine whether a certain protein shows the required biological activity. Proteins showing at least 70% and preferably at least 80% homology to the mature wild-type proteins of the above referenced protein families should be understood as encompassed by the present invention, as long as they contain the deletion or substitution of a cysteine, as required for the proteins according the invention, and therefore do not form dimers.

It is especially preferred that proteins according to the invention contain at least the 7 cysteine region characteristic for the TGF-β protein superfamily.

This specific 7 cysteine region is considered to be the most important part of the proteins in view of the biological activity. Therefore proteins retaining this critical region are preferred proteins according to the invention. It is disclosed in the state of the art which cysteine is responsible in a certain protein family or protein for dimer formation (see for example: Schlunegger & Grutter (1992) Nature 358, 430–434; Daopin et al., (1992) Science 257, 369–373 and Griffith et at., Proc. Natl. Acad. Sci. 93 (1996), page 878–883). This cysteine has to be deleted or substituted by another amino acid to form a protein according to the invention.

The 7 cysteine region is known for many proteins of the TGF-β protein superfamily. In this region the respective location of the cysteine residues to each other is important and is only allowed to vary slightly in order not to lose the biological activity. Consensus sequences for such proteins ar known in the state of the art and all proteins complying with such consensus sequences are considered to be encompassed by the present invention.

In an especially preferred embodiment of the present invention the protein contains a consensus sequence according to the following sequence (SEQ ID NO: 9)

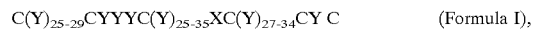

$$C(Y)_{25-29}CYYYC(Y)_{25-35}XC(Y)_{27-34}CY\ C \quad \text{(Formula I)},$$

wherein C denotes cysteine, Y denotes any amino acid including cysteine and X denotes any amino acid except cysteine.

More preferably the protein according to the invention contains a consensus sequence according to the following sequence (SEQ ID NO: 10)

$$C(Y)_{28}CYYYC(Y)_{30-32}XC(Y)_{31}CYC \quad \text{(Formula II)},$$

wherein C, X and Y have the same meaning as defined above.

Even more preferably the protein according to the invention contains a consensus sequence according to the following sequence (SEQ ID NO: 11)

$$C(X)_{28}CXXXC(X)_{31-33}C(X)_{31}CXC \quad \text{(Formula III)},$$

wherein C and X have the same meaning as defined above.

In these consensus sequences especially preferred distances between the respective cysteine residues are contained, wherein also already the dimer forming cysteine is substituted by another amino acid. As with all proteins of said protein superfamily the location of and distance between the cysteines is more important than the identity of the other amino acids contained in this region. Therefore, the consensus sequence shows the respective location of the cysteines, but does not show the identity of the other amino acids, since these other amino acids are widely variable in the proteins of the TGF-β protein superfamily.

In a preferred embodiment of the present invention the monomeric protein according to the invention is a morphogenetic protein.

Most of the members of the TGF-β protein superfamily are morphogenetic proteins that are useful for treatments where regulation of differentiation and proliferation of cells or progenitor cells is of interest. This can result in replacement of damaged and/or diseased tissue like for example skeletal (bone, cartilage) tissue, connective tissue, periodontal or dental tissue, neural tissue, tissue of the sensory system, liver, pancreas, cardiac, blood vessel and renal tissue, uterine or thyroid tissue etc. Morphogenetic proteins are often useful for the treatment of ulcerative or inflammatory tissue damage and wound healing of any kind such as enhanced healing of ulcers, burns, injuries or skin grafts. Especially preferred proteins according to the invention belong to the TGF-β, BMP, GDF, activin or GDNF families. Several BMP proteins which were originally discovered by their ability to induce bone formation, have been described, as also indicated above. Meanwhile, several additional functions have been found as it is also true for members of the GDFs. These proteins show a very broad field of applications and especially are in addition to their bone and cartilage growth promoting activity (see for example: WO 88/00205, WO 90/11366, WO 91/05802) useful in periodontal disease, for inhibiting periodontal and tooth tissue loss, for sealing tooth cavities, for enhancing integration of a tooth in a tooth socket (see for example: WO 96/26737, WO 94/06399, WO 95/24210), for connective tissue such as tendon or ligament (see for example: WO 95/16035), for improving survival of neural cells, for inducing growth of neural cells and repairing neural defects, for damaged CNS tissue due to stroke or trauma (see for example: WO 97/34626, WO 94/03200, WO 95/05846), for maintaining or restoring sensory perception (see for example WO 98/20890, WO 98/20889), for renal failure (see for example: WO 97/41880, WO 97/41881), for liver regeneration (see for example WO 94/06449), for regeneration of myocardium (see for example WO 98/27995), for treatment or preservation of tissues or cells for organ or tissue transplantation, for integrity of gastrointestinal lining (see for example WO 94/06420), for increasing progenitor cell population as for example hematopoietic progenitor cells by ex vivo stimulation (see for example WO 92/15323), etc. One preferred member of the GDF family is the protein MP52 which is also termed GDF-5 or CDMP-1. Applications for MP52 reflect several of the already described applications for the BMP/GDF family. MP52 is considered to be a very effective promoter of bone and cartilage formation as well as connective tissue formation (see for example WO 95/04819, Hötten et al., (1996), Growth Factors 13, 65–74, Storm et al., (1994) Nature 368, 639–643, Chang et al., (1994) J. Biol. Chem. 269 (45), 28227–28234). In this connection MP52 is useful for applications concerning the joints between skeletal elements (see for example Storm & Kingsley (1996) Development 122, 3969–3979). One example for connective tissue is tendon and ligament (Wolfman et al., (1997), J. Clin. Invest. 100, 321–330, Aspenberg & Forslund (1999), Acta Orthop Scand 70, 51–54, WO 95/16035). MP52 is also useful for tooth (dental and periodontal) applications (see for example WO 95/04819, WO 93/16099, Morotome et al. (1998), Biochem Biophys Res Comm 244, 85–90). MP52 is useful in wound repair of any kind. It is in addition very useful for promoting tissue growth in the neuronal system and survival of dopaminergic neurons, for example. MP52 in this connection is useful for applications in neurodegenerative diseases like e.g. Parkinson's disease and possibly also Alzheimer's disease for Huntington chorea tissues (see for example WO 97/03188, Krieglstein et al., (1995) J. Neurosci Res. 42, 724–732, Sullivan et al., (1997) Neurosci Lett 233, 73–76, Sullivan et al. (1998), Eur. J. Neurosci 10, 3681–3688). MP52 allows to maintain nervous function or to retain nervous function in already damaged tissues. MP52 is therefore considered to be a generally applicable neurotrophic factor. It is also useful for diseases of the eye, in particular retina cornea and optic nerve (see for example WO 97/03188, You et al. (1999), Invest Opthalmol Vis Sci 40, 296–311). The monomeric MP52 is expected to show all the already described activities of the dimeric form as well as some further described activities as described for the dimeric BMP/GDF family members. It is expected to be for example also useful for increasing progenitor cell populations and for stimulating differentiation of progenitor cells ex vivo. Progenitor cells can be cells which take part in the cartilage formation process or hematopoietic progenitor cells. It is also useful for damaged or diseased tissue where a stimulation of angiogenesis is advantageous (see for example: Yamashita et al. (1997), Exp Cell Res 235, 218–226).

An especially preferred protein according to the invention therefore is protein MP52 or a biologically active part or variant thereof. Like in the already above mentioned definition of these terms MP52 can e.g. be used in its mature form, however, it can also be used as a fragment thereof at least containing the 7 cysteine region or also in a precursory form. Deviations at the N-terminal part of mature MP52 do not affect its activity to a considerable degree. Therefore, substitutions, deletions or additions on the N-terminal part of the proteins are still within the scope of the present invention. It might be useful to add a peptide to the N-terminal part of the protein, e.g. for purification reasons. It might not be necessary to cleave off this added peptide after expression and purification of the protein. Additional peptides at the N- or C-terminal part of the protein may also serve for the targeting of the protein to special tissues such as nerve or bone tissue or for the penetration of the blood/brain barrier. Generally, also fusion proteins of a monomeric protein according to the invention and another peptide or group are considered within the scope of the present invention, wherein these other peptides or groups are directing the localization of the fusion protein, e.g. because of an affinity to a certain tissue type etc. Examples for such fusion proteins are described in WO 97/23612. The protein containing such addition will retain its biological activity at least as long as such addition does not impair the formation of the biologically active conformation of the protein.

In an especially preferred embodiment of the present invention the proteins comprises the amino acid sequence according to SEQ.ID.NO.1 (DNA and protein sequence) and SEQ.ID.No.2 (protein sequence, only), respectively. SEQ.ID.NO.2 shows the complete protein sequence of the prepro protein of human MP52, as already disclosed in WO 95/04819. The start of the mature protein lies preferably in the area of amino acids 352–400, especially preferred at amino acids 381 or 382. Therefore, the mature protein comprises amino acids 381–501 or 382–501. The first alanine of the mature protein can be deleted and the mature protein then preferably comprises amino acids 383–501. The cysteine at position 465 that is present in the already described dimeric MP52 protein is according to the invention either deleted or substituted by another amino acid. This deletion or substitution is represented by Xaa at the respective position in SEQ.ID.Nos.1 and 2.

The activin/inhibin family proteins are of interest for applications related to contraception, fertility and pregnancy (see for example WO 94/19455, U.S. Pat. No. 5,102,868).

They are also of interest for applications like repair or prevention of diseases of the nervous system, they can be used in the repair of organ tissue such as liver and even in bone and cartilage, too. In this connection MP121 (activin βC) is especially useful in applications for growth or regeneration of damaged and/or diseased tissue, especially the liver tissue, neural tissue, skeletal tissue (see for example WO 96/01316, WO 98/22492 and WO 97/03188). MP121 is known to be predominantly expressed in the liver whereby the mRNA is markedly reduced after partial hepatectomy. MP121 is expected to regulate the liver mass (Zhang et al., Endocrine Journal 44 (1997), page 759–764). The monomeric MP121 shows all the already described activities of the dimeric form as well as some further described activities as described for the dimeric TGF-β superfamily members. It is for example also expected to be useful in treatment of ulceration (for example stomach ulceration) and useful for integrity of gastrointestinal lining and for stimulating differentiation of progenitor cells ex vivo, treatment or preservation of mammalian tissue or cells, e.g. for organ or tissue transplantation.

A further preferred protein according to the invention therefore is MP121, a member of the activin/inhibin protein family. Also for this protein a biologically active part or variant thereof is encompassed by the present invention according to the above defined rules. An especially preferred embodiment is shown in SEQ.ID.NO.3 (DNA and protein sequence) and SEQ.ID.NO.4 (protein sequence, only) respectively. SEQ.ID.NO.4 shows the complete amino acid sequence of the prepro protein of human MP121, that has already been disclosed in WO 96/01316. The start of the mature protein lies preferably between amino acids 217 and 247, most preferred at amino acid 237. A preferred mature protein therefore comprises the mature part of the protein starting at amino acid 237 and ending at amino acid 352. However, also the precursor protein comprising the whole shown amino acid sequence is encompassed by the present invention. The cysteine at position 316 is according to the invention either deleted or substituted by another amino acid, being represented by Xaa in SEQ.ID.Nos.3 and 4.

The amino acid by which the cysteine residue effecting the dimerization is substituted can be selected by any amino acid that does not impair the formation of a biologically active conformation. The amino acid is preferably selected from the group of alanine, serine, threonine, leucine, isoleucine, glycine and valine.

The proteins according to the invention are in summary characterized by the absence of the cysteine residue in the amino acid sequence responsible for the dimer formation. This absence can be effected by substitution of this cysteine by another amino acid or by deletion. In case of deletion, however, it must be assured for the protein that the formation of the biologically active conformation is not hindered. The same is true for the selection of the substitution amino acid, wherein it is preferred to use an amino acid which has a form similar to cysteine.

The monomeric proteins according to the invention can be easily produced, in particular by expression in prokaryots and renaturation according to known methods. It is advantageous that the protein can be obtained in exceedingly biologically active form. The proteins exhibit in monomeric form about the same activity as the dimer so that based on the amount of active substance only the same amount of the monomeric protein has to be used in order to obtain the same positive biological effects.

A further subject matter of the present invention is a nucleic acid encoding a protein according to the invention.

It is obvious that the nucleic acid has to have such a sequence that a deletion or substitution of the cysteine responsible for the dimer formation is achieved. The nucleic acid can be a naturally occurring nucleic acid, but also a recombinantly produced or processed nucleic acid. The nucleic acid can be both a DNA sequence and an RNA sequence, as long as the protein according to the invention can be obtained from this nucleic acid upon expression in a suitable system.

In a preferred embodiment of the invention the nucleic acid is a DNA sequence. This DNA sequence in an especially preferred embodiment of the invention comprises a sequence as shown in SEQ.ID.NO.1 and SEQ.ID.NO.3, respectively, or parts thereof. SEQ.ID.NO.1 shows a nucleic acid encoding MP52, wherein the codon for the cysteine responsible for the dimer formation is replaced by another codon which does not encode cysteine or deleted. This substitution or deletion is shown as "nnn" in th sequence protocols. SEQ.ID.NO.3 shows a nucleic acid encoding MP121, wherein also the codon for the cysteine effecting the dimer formation is replaced by a respective different codon or deleted. Instead of the complete sequences of SEQ.ID.NOs.1 or 3 also parts can be used that encode the mature proteins or fragments also described above.

It is preferred in the framework of the present invention that the nucleic acid apart from the coding sequences also contains expression control sequences. Such expression control sequences are known to the man skilled in the art and serve to control the expression of the encoded protein in a host cell. The host cell does not have to be an isolated cell, moreover, the nucleic acid can be expressed in the patient in vivo in the target tissue. This can be done by inserting the nucleic acid into the cell genome, however, it is also possible to transform host cells with expression vectors containing a nucleic acid according to the invention. Such expression vectors are a further subject matter of the present invention, wherein the nucleic acid is inserted in a suitable vector system, the vector system being selected according to the desired expression of the protein. The vector system can be a eukaryotic vector system, but—in the framework of the present invention—it is preferably a prokaryotic vector system, with which the proteins can be produced in prokaryotic host cells in a particularly easy and pure manner. In addition, the expression vector can be a viral vector.

Also host cells in turn are a further subject matter of the present invention. The host cells are characterized in that they contain a nucleic acid according to the invention or an expression vector according to the invention and that they are able to use the information present in the nucleic acids and in the expression vector, respectively, for the expression of a monomeric protein according to the invention.

Although in the framework of the present invention also eukaryotic host cells are suitable for the production of the protein, it is, as mentioned already several times above, particularly advantageous that the protein according to the invention can be produced in prokaryotic host cells, which therefore represent a preferred embodiment of the present invention.

After such preferred expression in prokaryotic host cells the protein is purified and renatured according to known methods, thereby effecting intramolecular cystine bridge formation.

Since, however, not only in vitro production of the monomeric protein is possible, but also in vivo expression of a nucleic acid according to the invention, a further preferred embodiment is a eukaryotic host cell, and especially a eukaryotic host cell containing the DNA in its genome, or as an expression vector. Such host cell can also be useful for application to an individual in need of morphogenic treatment.

Further subject matters of the present application are pharmaceutical compositions comprising at least one monomeric protein according to the invention or at least one nucleic acid encoding for such a protein or at least one corresponding expression vector, or at least one eukaryotic host cell expressing the monomeric protein.

The protein itself, but also a nucleic acid according to the invention, an expression vector or a host cell can be considered to be advantageous as active substances in a pharmaceutical composition. Also combinations of monomeric proteins, with either biological activities in the same or different applications, can be used in preferred pharmaceutical compositions. Especially preferred for neuronal applications are combinations of MP52 with other TGF-β superfamily proteins, both in monomeric form, like for example with GDNF (see WO 97/03188). Also preferred for neuronal applications are combinations of TGF-β with GDNF, both in monomeric form. Also for applications concerning cartilage and/or bone the combination of several monomeric proteins might be useful, like MP52 with a protein of TGF-β (see e.g. WO 92/09697) or MP52 with a cartilage maintenance-inducing protein such as BMP-9 (see e.g. WO 96/39170). When a nucleic acid or an expression vector is used, however, it has to be ensured that when administering to the patient there has to be an environment in which the nucleic acid and the expression vector, respectively, can be expressed and the protein according to the invention can be produced in vivo at the site of action. The same applies accordingly to the host cell according to the invention. When using expression vectors or host cells it is also possible that they encode more than one monomeric protein of the invention to produce a combination of two or more monomeric proteins.

It is advantageous to both the protein and the nucleic acid or the expression vector or the host cell when they are applied in and/or on a biocompatible matrix. The matrix material can be transplanted into the patient, e.g. surgically, wherein the protein either is effective on the surface of the matrix material or the protein or the DNA encoding the protein can be slowly released from the matrix material and then be effective over a long period of time. Additionally it is possible and advantageous to use a biodegradable matrix material in the pharmaceutical composition, wherein this material preferably dissolves during the protein induced tissue formation so that a protein or a nucleic acid contained therein is released and the newly formed tissue replaces the matrix material.

Finally, in case of applications relating to bone formation, it is advantageous to use a matrix material which is itself e.g. osteogenically active. By using such a matrix material it becomes possible to achieve a synergistic effect of protein and matrix material and to effect a particularly rapid and effective bone formation.

An especially preferred matrix material that can be used according to the invention is a matrix material as described in U.S. Pat. No. 5,231,169 and U.S. Pat. No. 5,776,193 and especially for applications like spinal fusion.

When using a combination of a matrix material and protein and/or nucleic acid and/or expression vector, it is preferable to sterilize such a combination prior to its use. The matrix and the morphogenetic protein can be separately sterilized and then combined, but it is preferred to terminally sterilize the device consisting of matrix and morphogenetic protein. Terminal sterilization can be achieved by ionizing radation as already described for dimeric proteins (U.S. Pat. No. 5,674,292) but it is also advantageous to use ethylene oxide.

Of course this invention also comprises pharmaceutical compositions containing further substances like e.g. pharmacologically acceptable auxiliary and carrier substances. However, the protein according to th invention, also in case a matrix material is used, does not necessarily have to be used together with this matrix material, but can also be administered systemically, wherein it concentrates preferably in the surrounding of an implanted matrix material.

For some applications the protein according to the invention and the nucleic acid forming this protein, respectively or the expression vector or host cell can preferably be present in an injectable composition. Implants are not necessary or possible for every form of application of the proteins according to the invention. However, it is also possible to provide an implantable vessel or an implantable micropump containing for example semipermeable membranes in which the protein according to the invention or the nucleic acid generating it is contained, from which either one is slowly released over a prolonged period of time. The pharmaceutical composition according to the invention can also contain other vehicles which make it possible that the proteins or the nucleic acids or the expression vectors encoding these proteins be transported to the site of activity and released there, wherein e.g. liposomes or nanospheres can be used. In principle, it is also possible to apply host cells, like e.g. implanted embryonic cells expressing the proteins. Cells transfected with recombinant DNA may be encapusled prior to implantation. Any other practicable but herein not explicitly described form of application of the pharmaceutical composition according the invention and their corresponding manufacture are also comprised by the present invention, as long as they contain a protein according to the invention or a nucleic acid or an expression vector coding therefor, or a host cell expressing it.

Although the indications shall not be restricted herein and all indications exhibiting the dimeric form of the protein according to the invention are also comprised, in the following types of application for the compositions according to the invention are listed which are considered to be particularly preferred indications for the proteins of the present invention. On the one hand, there is the prevention or therapy of diseases associated with bone and/or cartilage damage or affecting bone and/or cartilage disease, or generally situations, in which cartilage and/or bone formation is desirable or for spinal fusion, and on the other hand, there is prevention or therapy of damaged or diseased tissue associated with connective tissue including tendon and/or ligament, periodontal or dental tissue including dental implants, neural tissue including CNS tissue and neuropathological situations, tissue of the sensory system, liver, pancreas, cardiac, blood vessel, renal, uterine and thyroid tissue, skin, mucous membranes, endothelium, epithelium, for promotion or induction of nerve growth, tissue regeneration, angiogenesis, wound healing including ulcers, burns, injuries or skin grafts, induction of proliferation of progenitor cells or bone marrow cells, for maintenance of a state of proliferation or differentiation for treatment or preservation of tissue or cells for organ or tissue transplantation, for integrity of gastrointestinal lining, for treatment of disturbances in fertility, contraception or pregnancy.

Diseases concerning sensory organs like the eye are also to be included in the preferred indication of the pharmaceutical composition according to the invention. As neuronal diseases again Parkinson's and Alzheimer's diseases can be mentioned as examples.

The pharmaceutical compositions according to the invention can be used in any desired way, the pharmaceutical compositions ar formulated preferably for surgical local application, topical or systemic application. Auxiliary substances for the individual application form can of course be present in the pharmaceutical composition according to the invention. For some applications it can be advantageous to add some further substances to the pharmaceutical composition as for example Vitamin D (WO 92/21365), parathyroid hormone related peptide (WO 97/35607), chordin (WO 98/21335), anti-fibrinolytic agent (EP 535091), anti-metabolites (WO 95/09004), alkyl cellulose (WO 93/00050), mannitol (WO 98/33514), sugar, glycine, glutamic acid hydrochloride (U.S. Pat. No. 5,385,887), antibiotics, antiseptics, amino acids and/or additives which improve the solubility or stablility of the monomeric morphogenetic protein as for example nonionic detergents (e.g. Tween 80), basic amino acids, carrier proteins (e.g. serum albumin), full length propeptides of the TGF-β superfamily or parts thereof.

As can be already gathered from the description of proteins, nucleic acids and pharmaceutical compositions, the proteins according to the invention and respective nucleic acids, which provide for an expression of the proteins at the site of activity, can advantageously be applied in all areas for which also the dimeric forms of the proteins, as described, can be applied. In the framework of the present invention therefore a further subject matter is the use of a pharmaceutical composition according to the present invention for the treatment or prevention of any indications of the dimeric forms of the proteins according to the invention.

Herein it is again possible to conduct surgical operations and to implant the pharmaceutical composition (in particular contained on a matrix material), an administration in liquid or otherwise suitable form via, e.g. injection or oral administration seems to be as suitable as a topical application for e.g. tissue regeneration.

FIG. 1A shows a two dimensional graph of the conformation of recombinantly produced dimeric MP52 (SEQ ID NO: 12) with the detected first alanine. In this figure the 7 cysteine bridges contained in a dimer are shown, wherein there are 3 intramolecular cystine bridges per monomer unit and 1 intermolecular cystine bridge connecting both monomers. FIG. 1B shows the monomeric protein (SEQ ID NO: 13) according to the invention wherein the cystein of the amino acid sequence of MP52 has been replaced by X that denotes any amino acid except cysteine.

EXAMPLES

The examples shall explain the invention more illustratively and are not considered to be restrictive.

Expression of monomeric MP52 in E. coli, refolding, purification and possible test systems to determine the biological activity.

The mature part of human MP52 was mutated by converting Cysteine to Alanine at position 465 of SEQ ID NO 2. For this purpose the nucleotides at the position 2032 and 2033 of SEQ ID NO 1 were converted from TG to GC. The substitution of the nucleotides was performed by using the prokaryotic plasmid pBP2 MP52m and a PCR method.

The vector pBP2 MP52m is a derivative of the pBR322 plasmid containing an ampicillin resistance gene, a T7-promoter followed by a ribosomal binding site, a start codon, the mature part of MP52 (coding for the amino acids 382–501 in SEQ ID NO. 2 with a Cysteine at position 465), stop codons in each reading frame and a terminator. The plasmid was deposited at the DSM (DSM 10029, 2nd Jun. 1995).

The mutation was performed by using the Quick-Change™ Site-Directed Mutagenesis Kit with the Pfu Turbo™ DNA polymerase and the Dpn I endonuclease from Stratagene (Catalog #200518) according to the instruction manual of the manufacturer. The oligonucleotide CCACAC-CACCCACCGCCTGTGTGCCCACGC (SEQ ID NO. 5) and the oligonucleotide GCGTGGGCACACAGGCG-GTGGGTGGTGTGG (SEQ ID NO. 6) were purified by polyacrylamide gel electrophoresis and used as the mutagenic primers. The resulting plasmid pBP2 MP52$_{ALA}$ contained after the start codon the nucleotide sequence coding for the amino acids 382–501 in SEQ ID NO. 2 with an Alanine at position 465 which was verified by sequencing.

The expression of monomeric MP52 can be induced by providing a source of T7 RNA polymerase. Using the bacterial strain BL21 (DE3)pLysS (Novagen) transformed with the plasmid pBP2 MP52$_{ALA}$ and inducing the T7 RNA polymerase gene according to the manufacturers instructions with IPTG, monomeric MP52 can be expressed in inclusion bodies which can be isolated according to standard procedures. Further purification was done on a reversed phase column (Nucleosil 300–7C4, Machery-Nagel) with a 0 to 50% buffer B gradient (buffer A: 0.1% TFA in water, buffer B: 90% acetonitrile, 0.1% TFA) in 50 minutes (flow rate: 2 ml/min). The fractions containing monomeric MP52 were pooled, lyophilized and stored at −70° C. MP52 was solubilized in a denaturing buffer (6M Urea, 500 mM NaCl, 10 mM DTT, 1 mM EDTA, 20 mM Tris pH 8.3) and added for refolding in 9 times of a 50 mM Glycine-buffer system (pH 9.8) containing CHAPS (20 mM), NaCl (500 mM) and 3 mM GSSG and gently stirred at 4° C. After approximately 24 hours the sample was diluted 2.8 times with 14 mM NaH$_2$PO$_4$ and subjected to isoelectric precipitation. After centrifugation the precipitate was dissolved in 0.1% TFA and the folded monomer was further purified by reversed phase HPLC. For this purpose MP52 was loaded on a column (Aquapore Octyl 20 micron, Applied Biosystems) equilibrated with 25% buffer B (buffer A: 0.1% TFA in water, buffer B: 90% acetonitrile, 0.1% TFA). Monomeric MP52 was eluted with a 25–60% buffer B gradient in 70 minutes (flow rate 3 ml/min). Fractions containing purified refolded monomeric MP52 were pooled, lyophilized, stored at −70° C. and can be used in biological activity studies. Useful for biological activity studies of monomeric MP52 in the field of cartilage and bone induction are for example the measurement of increasing ALP activity (Takuwa et al., Am. J. Physiol. 257, E797–E803, 1989) using osteoprogenitor-like ROB-C26 cells (Yamaguchi et al., Calcif. Tissue Int. 49, 221–225, 1991) as described in WO95/04819 or ATDC5 cells (Riken Gene Bank, RCB 0565, embryonic cells which differentiate like cartilage cells). Useful activity tests showing the neurological capacities of refolded monomeric MP52 are the measurement of increased survival of dopaminergic neurons as described for example by Krieglstein et al. (J. Neuroscience Res. 42, 724–732, 1995) or Sullivan et al. (Neuroscience Letters 233, 73–76, 1997) or the outgrowth of nerve fibers from embryonic retina are described for example in the WO 97/03188. The angiogenic potential of folded monomeric MP52 can be verified for example in an in vivo corneal micropocket model. Briefly, Hydron can be used as a slow release pellet adapted from D'Amato et al (Proc. Natl. Acad. Sci. USA 91 (1994) 4082–4085). About 2 μg of monomeric MP52 can be dissolved in 20 μl of 50% acetonitrile, stabilized with 5 mg sucralfate (sucrose aluminum sulfate; Bukh Meditec, Copenhagen) and mixed with 20 μl of 12% (wt/vol) Hydron NCC (Interferon Science, New Brunswick, N.J.) in ethanol. The mixture can be pipetted onto Teflon pegs and dried to produce a pellet. Subsequently the pellet can be implanted into corneal micropockets of the eye of a male New Zealand White rabbit. For this purpose an intrastromal tunnel, starting from a perpendicular linear incision in the pupillary plane and ending 2.75 mm prior to the limbus can be created. As a postsurgical care one single dose of erythromycin ointment should be given onto the surface of the cornea. About 10 days after implantation new capillaries which grow toward the implantation site should be seen. The outgrowth towards the pellet can reflect the chemotactic response of the endothelial cells to the released MP52 and can be quantified by measuring the vascularized area and the number of vessels at the limbus.

Monomeric MP52 isolated and purified from inclusion bodies but not subjected to the refolding process can be used as a negative control. Dimeric MP52 can be used as the positive control.

Expression of monomeric MP121 in E. coli, refolding, purification and possible test systems to determine the biological activity.

The mature part of human MP121 was mutated by converting Cysteine to Alanine at position 316 of SEQ ID NO 4. For this purpose the nucleotides at position 1073 and 1074 of SEQ ID NO. 3 were converted from TG to GC. The substitution of the nucleotides was performed essentially as described for MP52 in the above example with differences in the plasmid and the mutagenic primers. The pBP4 MP121m plasmid was used which differs from the pBP2 MP52m plasmid by containing the mature part of MP121 (coding for the amino acids 237–352 in SEQ ID NO. 4 with a Cysteine at position 316) instead of the mature part of MP52 and by harboring a tetracycline resistance gene instead of the ampicillin resistance gene. As mutagenic primers the oligonucleotide CTGGAGGGGGCTCAGCCTGTGTACCCACGG (SEQ ID NO. 7) and the oligonucleotide CCGTGGGTACACAGGCTGAGCCCCCTCCAG (SEQ ID NO. 8) were used.

The resulting plasmid pBP4 MP121$_{ALA}$ contained after the start codon the nucleotide sequence coding for the amino acids 237–352 in SEQ ID NO. 4 with an Alanine at position 316 which was verified by sequencing.

The expression of monomeric MP121, isolation of inclusion bodies and purification was performed essentially as described for MP52 in the above example, with the exception that another E. coli strain, the HMS 174 (DE3) (Novagen), was used.

For biological activity studies of refolded monomeric MP121 showing the neurological capacities the same assays as mentioned for MP52 can be used. The influence of refolded monomeric MP121 on liver growth can be investigated for example on rat hepatocytes in primary cultures by inhibiting EGF induced DNA synthesis. Briefly, hepatocytes can be isolated from rat (Wistar) liver and cultured according to Yasuda et al. (J. Clin. Invest. Vol. 92, 1491–1496 (1993)). The cells have to be washed prior to incubation with fresh serum-free medium containing 0.1 nM insulin. 0.1% BSA and 1 nM EGF. The solubilized refolded monomeric MP121 can be added to the medium at various concentrations and subsequently the hepatocytes have to be incubated for 72 h including 0.5 μCi [$^3$H]Thymidine/ml for the last 24 hours as described by Mead & Fausto (Proc. Natl.Acad. .Sci.USA 86, 1558–15562 (1989)). [$^3$H]Thymidine incorporation into trichloracetic acid-precitable material can be measured as described by McNiel et al. (J. Cell Biol. 101, 372–379 (1985)).

Stimulation of hematopoiesis can be determined for examples on bone marrow aspirate cultures as described in example 8 of WO98122492.

What is claimed is:

1. Protein MP52, characterized in that the protein has no cysteine responsible for dimer formation and
   a) (i) comprises the amino acid sequence CSRKALHVNFKDMGWDDWIIAPLEYEAFHCEGLCEFPLRSHLEPTNHAVIQTLMNSMDP ESTPPTXCVPTRLSPISILFIDSANNVVYKQYEDMVVESCGC (SEQ ID NO: 14) wherein X denotes any amino acid except cysteine, and
      (ii) promotes at least bone or cartilage formation,
   or
   b) is a mature protein or a biologically active part promoting at least bone or cartilage formation.

2. Protein according to claim 1, characterized in that it comprises the amino acid sequence according to SEQ.ID.NO.2 or a part thereof.

3. Protein according to claim 1, wherein X is selected from the group consisting of alanine, serine, threonine, leucine, isoleucine, glycine and valine.

4. Protein according to claim 1, characterized in that it contains additional amino acids that facilitate or mediate the transfer and localization of the protein in a certain tissue.

5. Pharmaceutical composition, characterized in that it contains at least one protein according to claim 1.

6. Pharmaceutical composition according to claim 5, characterized in that the protein is contained at least in or on a biocompatible matrix material.

7. Pharmaceutical composition according to claim 6, characterized in that the matrix material is biodegradable.

8. Pharmaceutical composition according to claim 6, characterized in that the matrix material is itself osteogenically active.

9. Pharmaceutical composition according to claim 5 for surgical local application, topical or systemic application.

10. Pharmaceutical composition according to claim 5 characterized in that it further contains pharmacologically acceptable auxiliary substances.

11. Pharmaceutical composition according to claim 9, characterized in that the composition is injectable.

12. Pharmaceutical composition according to claim 9, characterized in that it is contained in a vehicle that allows it to direct and release the composition to a determined site of action.

13. Pharmaceutical composition according to claim 12, characterized in that the vehicle is selected from liposomes, nanospheres, larger implantable containers and micropumps.

14. The protein of claim 1, wherein said protein is in monomeric form.

15. The protein of claim 1, wherein said protein has the amino acid sequence CSRKALHVNFKDMGWDDWIIAPLEYEAFHCEGLCEFPLRSHLEPTNHAVIQTLMNSMDP ESTPPTXCVPTRLSPISILFIDSANNVVYKQYEDMVVESCGC (SEQ ID NO: 14), wherein X denotes any amino acid except cysteine.

* * * * *

UNITED STATES PATENT AND TRADEMARK OFFICE
CERTIFICATE OF CORRECTION

PATENT NO. : 6,972,321 B1  
APPLICATION NO. : 10/048458  
DATED : December 6, 2005  
INVENTOR(S) : Hötten et al.

Page 1 of 1

It is certified that error appears in the above-identified patent and that said Letters Patent is hereby corrected as shown below:

ON THE TITLE PAGE:
(87)   PCT Pub. Date:          February 15, 2001

Col. 11, line 42:          Please delete the word "detected" and substitute the word "deleted".

Signed and Sealed this

Twenty-fifth Day of July, 2006

JON W. DUDAS  
*Director of the United States Patent and Trademark Office*

SEQUENCE LISTING

<160> NUMBER OF SEQ ID NOS: 14

<210> SEQ ID NO 1
<211> LENGTH: 2703
<212> TYPE: DNA
<213> ORGANISM: Homo sapiens
<220> FEATURE:
<221> NAME/KEY: CDS
<222> LOCATION: (640)..(2142)
<220> FEATURE:
<221> NAME/KEY: misc_feature
<222> LOCATION: (2032)..(2034)
<223> OTHER INFORMATION: n = any nucleotide

<400> SEQUENCE: 1

```
ccatggcctc gaaagggcag cggtgatttt tttcacataa atatatcgca cttaaatgag      60
tttagacagc atgacatcag agagtaatta aattggtttg ggttggaatt ccgtttccaa     120
ttcctgagtt caggtttgta aaagattttt ctgagcacct gcaggcctgt gagtgtgtgt     180
gtgtgtgtgt gtgtgtgtgt gtgtgtgtga agtattttca ctggaaagga ttcaaaacta     240
gggggaaaaa aaaactggag cacacaggca gcattacgcc attcttcctt cttggaaaaa     300
tccctcagcc ttatacaagc ctccttcaag ccctcagtca gttgtgcagg agaaaggggg     360
cggttggctt tctcctttca agaacgagtt attttcagct gctgactgga gacggtgcac     420
```

```
                                                                      -continued gtctggatac gagagcattt ccactatggg actggataca acacacacc cggcagactt       480 caagagtctc agactgagga gaaagccttt ccttctgctg ctactgctgc tgccgctgct      540
tttgaaagtc cactcctttc atggttttc ctgccaaacc agaggcacct ttgctgctgc       600
cgctgttctc tttggtgtca ttcagcggct ggccagagg atg aga ctc ccc aaa         654
                                            Met Arg Leu Pro Lys
                                            1                5 ctc ctc act ttc ttg ctt tgg tac ctg gct tgg ctg gac ctg gaa ttc        702
Leu Leu Thr Phe Leu Leu Trp Tyr Leu Ala Trp Leu Asp Leu Glu Phe
            10                  15                  20 atc tgc act gtg ttg ggt gcc cct gac ttg ggc cag aga ccc cag ggg        750
Ile Cys Thr Val Leu Gly Ala Pro Asp Leu Gly Gln Arg Pro Gln Gly
            25                  30                  35 acc agg cca gga ttg gcc aaa gca gag gcc aag gag agg ccc ccc ctg        798
Thr Arg Pro Gly Leu Ala Lys Ala Glu Ala Lys Glu Arg Pro Pro Leu
        40                  45                  50 gcc cgg aac gtc ttc agg cca ggg ggt cac agc tat ggt ggg ggg gcc       846
Ala Arg Asn Val Phe Arg Pro Gly Gly His Ser Tyr Gly Gly Gly Ala
    55                  60                  65 acc aat gcc aat gcc agg gca aag gga ggc acc ggg cag aca gga ggc       894
Thr Asn Ala Asn Ala Arg Ala Lys Gly Gly Thr Gly Gln Thr Gly Gly
70                  75                  80                  85 ctg aca cag ccc aag aag gat gaa ccc aaa aag ctg ccc ccc aga ccg       942
Leu Thr Gln Pro Lys Lys Asp Glu Pro Lys Lys Leu Pro Pro Arg Pro
                90                  95                  100 ggc ggc cct gaa ccc aag cca gga cac cct ccc caa aca agg cag gct       990
Gly Gly Pro Glu Pro Lys Pro Gly His Pro Pro Gln Thr Arg Gln Ala
            105                 110                 115 aca gcc cgg act gtg acc cca aaa gga cag ctt ccc gga ggc aag gca       1038
Thr Ala Arg Thr Val Thr Pro Lys Gly Gln Leu Pro Gly Gly Lys Ala
        120                 125                 130 ccc cca aaa gca gga tct gtc ccc agc tcc ttc ctg ctg aag aag gcc       1086
Pro Pro Lys Ala Gly Ser Val Pro Ser Ser Phe Leu Leu Lys Lys Ala
    135                 140                 145 agg gag ccc ggg ccc cca cga gag ccc aag gag ccg ttt cgc cca ccc       1134
Arg Glu Pro Gly Pro Pro Arg Glu Pro Lys Glu Pro Phe Arg Pro Pro
150                 155                 160                 165 ccc atc aca ccc cac gag tac atg ctc tcg ctg tac agg acg ctg tcc       1182
Pro Ile Thr Pro His Glu Tyr Met Leu Ser Leu Tyr Arg Thr Leu Ser
                170                 175                 180 gat gct gac aga aag gga ggc aac agc agc gtg aag ttg gag gct ggc       1230
Asp Ala Asp Arg Lys Gly Gly Asn Ser Ser Val Lys Leu Glu Ala Gly
            185                 190                 195 ctg gcc aac acc atc acc agc ttt att gac aaa ggg caa gat gac cga       1278
Leu Ala Asn Thr Ile Thr Ser Phe Ile Asp Lys Gly Gln Asp Asp Arg
        200                 205                 210 ggt ccc gtg gtc agg aag cag agg tac gtg ttt gac att agt gcc ctg       1326
Gly Pro Val Val Arg Lys Gln Arg Tyr Val Phe Asp Ile Ser Ala Leu
    215                 220                 225 gag aag gat ggg ctg ctg ggg gcc gag ctg cgg atc ttg cgg aag aag       1374
Glu Lys Asp Gly Leu Leu Gly Ala Glu Leu Arg Ile Leu Arg Lys Lys
230                 235                 240                 245 ccc tcg gac acg gcc aag cca gcg gcc ccc gga ggc ggg cgg gct gcc       1422
Pro Ser Asp Thr Ala Lys Pro Ala Ala Pro Gly Gly Gly Arg Ala Ala
                250                 255                 260 cag ctg aag ctg tcc agc tgc ccc agc ggc cgg cag ccg gcc tcc ttg       1470
Gln Leu Lys Leu Ser Ser Cys Pro Ser Gly Arg Gln Pro Ala Ser Leu
            265                 270                 275
```

```
ctg gat gtg cgc tcc gtg cca ggc ctg gac gga tct ggc tgg gag gtg      1518
Leu Asp Val Arg Ser Val Pro Gly Leu Asp Gly Ser Gly Trp Glu Val
        280                 285                 290 ttc gac atc tgg aag ctc ttc cga aac ttt aag aac tcg gcc cag ctg      1566
Phe Asp Ile Trp Lys Leu Phe Arg Asn Phe Lys Asn Ser Ala Gln Leu
    295                 300                 305 tgc ctg gag ctg gag gcc tgg gaa cgg ggc agg gcc gtg gac ctc cgt      1614
Cys Leu Glu Leu Glu Ala Trp Glu Arg Gly Arg Ala Val Asp Leu Arg
310                 315                 320                 325 ggc ctg ggc ttc gac cgc gcc gcc cgg cag gtc cac gag aag gcc ctg      1662
Gly Leu Gly Phe Asp Arg Ala Ala Arg Gln Val His Glu Lys Ala Leu
                330                 335                 340 ttc ctg gtg ttt ggc cgc acc aag aaa cgg gac ctg ttc ttt aat gag      1710
Phe Leu Val Phe Gly Arg Thr Lys Lys Arg Asp Leu Phe Phe Asn Glu
            345                 350                 355 att aag gcc cgc tct ggc cag gac gat aag acc gtg tat gag tac ctg      1758
Ile Lys Ala Arg Ser Gly Gln Asp Asp Lys Thr Val Tyr Glu Tyr Leu
        360                 365                 370 ttc agc cag cgg cga aaa cgg cgg gcc cca ctg gcc act cgc cag ggc      1806
Phe Ser Gln Arg Arg Lys Arg Arg Ala Pro Leu Ala Thr Arg Gln Gly
375                 380                 385 aag cga ccc agc aag aac ctt aag gct cgc tgc agt cgg aag gca ctg      1854
Lys Arg Pro Ser Lys Asn Leu Lys Ala Arg Cys Ser Arg Lys Ala Leu
390                 395                 400                 405 cat gtc aac ttc aag gac atg ggc tgg gac gac tgg atc atc gca ccc      1902
His Val Asn Phe Lys Asp Met Gly Trp Asp Asp Trp Ile Ile Ala Pro
                410                 415                 420 ctt gag tac gag gct ttc cac tgc gag ggg ctg tgc gag ttc cca ttg      1950
Leu Glu Tyr Glu Ala Phe His Cys Glu Gly Leu Cys Glu Phe Pro Leu
            425                 430                 435 cgc tcc cac ctg gag ccc acg aat cat gca gtc atc cag acc ctg atg      1998
Arg Ser His Leu Glu Pro Thr Asn His Ala Val Ile Gln Thr Leu Met
        440                 445                 450 aac tcc atg gac ccc gag tcc aca cca ccc acc nnn tgt gtg ccc acg      2046
Asn Ser Met Asp Pro Glu Ser Thr Pro Pro Thr Xaa Cys Val Pro Thr
455                 460                 465 cgg ctg agt ccc atc agc atc ctc ttc att gac tct gcc aac aac gtg      2094
Arg Leu Ser Pro Ile Ser Ile Leu Phe Ile Asp Ser Ala Asn Asn Val
470                 475                 480                 485 gtg tat aag cag tat gag gac atg gtc gtg gag tcg tgt ggc tgc agg      2142
Val Tyr Lys Gln Tyr Glu Asp Met Val Val Glu Ser Cys Gly Cys Arg
                490                 495                 500 tagcagcact ggccctctgt cttcctgggt ggcacatccc aagagcccct tcctgcactc    2202
ctggaatcac agaggggtca ggaagctgtg gcaggagcat ctacacagct tgggtgaaag    2262
gggattccaa taagcttgct cgctctctga gtgtgacttg gctaaaggc ccccttttat     2322 ccacaagttc cctggctga ggattgctgc ccgtctgctg atgtgaccag tggcaggcac     2382
aggtccaggg agacagactc tgaatgggac tgagtcccag gaaacagtgc tttccgatga    2442
gactcagccc accatttctc ctcacctggg ccttctcagc ctctggactc tcctaagcac    2502
ctctcaggag agccacaggt gccactgcct cctcaaatca catttgtgcc tggtgacttc    2562
ctgtccctgg acagttgag aagctgactg ggcaagagtg ggagagaaga ggagagggct     2622
tggatagagt tgaggagtgt gaggctgtta gactgttaga tttaaatgta tattgatgag    2682
ataaaaagca aaactgtgcc t                                              2703

<210> SEQ ID NO 2
<211> LENGTH: 501
```

```
<212> TYPE: PRT
<213> ORGANISM: Homo sapiens
<220> FEATURE:
<221> NAME/KEY: misc_feature
<222> LOCATION: (465)..(465)
<223> OTHER INFORMATION: Xaa = any amino acid

<400> SEQUENCE: 2
```

| | | | | | | | | | | | | | | |
|---|---|---|---|---|---|---|---|---|---|---|---|---|---|---|
| Met | Arg | Leu | Pro | Lys | Leu | Leu | Thr | Phe | Leu | Leu | Trp | Tyr | Leu | Ala | Trp |
| 1 | | | | 5 | | | | | 10 | | | | | 15 | |
| Leu | Asp | Leu | Glu | Phe | Ile | Cys | Thr | Val | Leu | Gly | Ala | Pro | Asp | Leu | Gly |
| | | | 20 | | | | | 25 | | | | | 30 | | |
| Gln | Arg | Pro | Gln | Gly | Thr | Arg | Pro | Gly | Leu | Ala | Lys | Ala | Glu | Ala | Lys |
| | 35 | | | | | 40 | | | | | 45 | | | | |
| Glu | Arg | Pro | Pro | Leu | Ala | Arg | Asn | Val | Phe | Arg | Pro | Gly | Gly | His | Ser |
| 50 | | | | | 55 | | | | | 60 | | | | | |
| Tyr | Gly | Gly | Gly | Ala | Thr | Asn | Ala | Asn | Ala | Arg | Ala | Lys | Gly | Gly | Thr |
| 65 | | | | | 70 | | | | 75 | | | | | | 80 |
| Gly | Gln | Thr | Gly | Gly | Leu | Thr | Gln | Pro | Lys | Lys | Asp | Glu | Pro | Lys | Lys |
| | | | | 85 | | | | | 90 | | | | | 95 | |
| Leu | Pro | Pro | Arg | Pro | Gly | Gly | Pro | Glu | Pro | Lys | Pro | Gly | His | Pro | Pro |
| | | | 100 | | | | | 105 | | | | | 110 | | |
| Gln | Thr | Arg | Gln | Ala | Thr | Ala | Arg | Thr | Val | Thr | Pro | Lys | Gly | Gln | Leu |
| | | 115 | | | | | 120 | | | | | 125 | | | |
| Pro | Gly | Gly | Lys | Ala | Pro | Pro | Lys | Ala | Gly | Ser | Val | Pro | Ser | Ser | Phe |
| | 130 | | | | | 135 | | | | | 140 | | | | |
| Leu | Leu | Lys | Lys | Ala | Arg | Glu | Pro | Gly | Pro | Pro | Arg | Glu | Pro | Lys | Glu |
| 145 | | | | | 150 | | | | | 155 | | | | | 160 |
| Pro | Phe | Arg | Pro | Pro | Ile | Thr | Pro | His | Glu | Tyr | Met | Leu | Ser | Leu |
| | | | | 165 | | | | | 170 | | | | | 175 |
| Tyr | Arg | Thr | Leu | Ser | Asp | Ala | Asp | Arg | Lys | Gly | Gly | Asn | Ser | Ser | Val |
| | | | 180 | | | | | 185 | | | | | 190 | | |
| Lys | Leu | Glu | Ala | Gly | Leu | Ala | Asn | Thr | Ile | Thr | Ser | Phe | Ile | Asp | Lys |
| | | 195 | | | | | 200 | | | | | 205 | | | |
| Gly | Gln | Asp | Asp | Arg | Gly | Pro | Val | Val | Arg | Lys | Gln | Arg | Tyr | Val | Phe |
| | 210 | | | | | 215 | | | | | 220 | | | | |
| Asp | Ile | Ser | Ala | Leu | Glu | Lys | Asp | Gly | Leu | Leu | Gly | Ala | Glu | Leu | Arg |
| 225 | | | | | 230 | | | | | 235 | | | | | 240 |
| Ile | Leu | Arg | Lys | Lys | Pro | Ser | Asp | Thr | Ala | Lys | Pro | Ala | Ala | Pro | Gly |
| | | | | 245 | | | | | 250 | | | | | 255 | |
| Gly | Gly | Arg | Ala | Ala | Gln | Leu | Lys | Leu | Ser | Ser | Cys | Pro | Ser | Gly | Arg |
| | | | 260 | | | | | 265 | | | | | 270 | | |
| Gln | Pro | Ala | Ser | Leu | Leu | Asp | Val | Arg | Ser | Val | Pro | Gly | Leu | Asp | Gly |
| | | 275 | | | | | 280 | | | | | 285 | | | |
| Ser | Gly | Trp | Glu | Val | Phe | Asp | Ile | Trp | Lys | Leu | Phe | Arg | Asn | Phe | Lys |
| | 290 | | | | | 295 | | | | | 300 | | | | |
| Asn | Ser | Ala | Gln | Leu | Cys | Leu | Glu | Leu | Glu | Ala | Trp | Glu | Arg | Gly | Arg |
| 305 | | | | | 310 | | | | | 315 | | | | | 320 |
| Ala | Val | Asp | Leu | Arg | Gly | Leu | Gly | Phe | Asp | Arg | Ala | Ala | Arg | Gln | Val |
| | | | | 325 | | | | | 330 | | | | | 335 | |
| His | Glu | Lys | Ala | Leu | Phe | Leu | Val | Phe | Gly | Arg | Thr | Lys | Lys | Arg | Asp |
| | | | 340 | | | | | 345 | | | | | 350 | | |
| Leu | Phe | Phe | Asn | Glu | Ile | Lys | Ala | Arg | Ser | Gly | Gln | Asp | Asp | Lys | Thr |
| | | 355 | | | | | 360 | | | | | 365 | | | |

```
Val Tyr Glu Tyr Leu Phe Ser Gln Arg Arg Lys Arg Arg Ala Pro Leu
    370             375             380
Ala Thr Arg Gln Gly Lys Arg Pro Ser Lys Asn Leu Lys Ala Arg Cys
385             390             395             400
Ser Arg Lys Ala Leu His Val Asn Phe Lys Asp Met Gly Trp Asp Asp
                405             410             415
Trp Ile Ile Ala Pro Leu Glu Tyr Glu Ala Phe His Cys Glu Gly Leu
            420             425             430
Cys Glu Phe Pro Leu Arg Ser His Leu Glu Pro Thr Asn His Ala Val
        435             440             445
Ile Gln Thr Leu Met Asn Ser Met Asp Pro Glu Ser Thr Pro Pro Thr
    450             455             460
Xaa Cys Val Pro Thr Arg Leu Ser Pro Ile Ser Ile Leu Phe Ile Asp
465             470             475             480
Ser Ala Asn Asn Val Val Tyr Lys Gln Tyr Glu Asp Met Val Val Glu
                485             490             495
Ser Cys Gly Cys Arg
            500

<210> SEQ ID NO 3
<211> LENGTH: 2272
<212> TYPE: DNA
<213> ORGANISM: Homo sapiens
<220> FEATURE:
<221> NAME/KEY: CDS
<222> LOCATION: (128)..(1183)
<220> FEATURE:
<221> NAME/KEY: misc_feature
<222> LOCATION: (1073)..(1075)
<223> OTHER INFORMATION: n = any nucleotide

<400> SEQUENCE: 3
caaggagcca tgccagctgg acacacactt cttccagggc ctctggcagc caggacagag      60
ttgagaccac agctgttgag accctgagcc ctgagtctgt attgctcaag aagggccttc     120 cccagca atg acc tcc tca ttg ctt ctg gcc ttt ctc ctc ctg gct cca       169
        Met Thr Ser Ser Leu Leu Leu Ala Phe Leu Leu Leu Ala Pro
        1               5                   10 acc aca gtg gcc act ccc aga gct ggc ggt cag tgt cca gca tgt ggg       217
Thr Thr Val Ala Thr Pro Arg Ala Gly Gly Gln Cys Pro Ala Cys Gly
15                  20                  25                  30 ggg ccc acc ttg gaa ctg gag agc cag cgg gag ctg ctt ctt gat ctg       265
Gly Pro Thr Leu Glu Leu Glu Ser Gln Arg Glu Leu Leu Leu Asp Leu
                35                  40                  45 gcc aag aga agc atc ttg gac aag ctg cac ctc acc cag cgc cca aca       313
Ala Lys Arg Ser Ile Leu Asp Lys Leu His Leu Thr Gln Arg Pro Thr
            50                  55                  60 ctg aac cgc cct gtg tcc aga gct gct ttg agg act gca ctg cag cac       361
Leu Asn Arg Pro Val Ser Arg Ala Ala Leu Arg Thr Ala Leu Gln His
        65                  70                  75 ctc cac ggg gtc cca cag ggg gca ctt cta gag gac aac agg gaa cag       409
Leu His Gly Val Pro Gln Gly Ala Leu Leu Glu Asp Asn Arg Glu Gln
80                  85                  90 gaa tgt gaa atc atc agc ttt gct gag aca ggc ctc tcc acc atc aac       457
Glu Cys Glu Ile Ile Ser Phe Ala Glu Thr Gly Leu Ser Thr Ile Asn
95                  100                 105                 110 cag act cgt ctt gat ttt cac ttc tcc tct gat aga act gct ggt gac       505
Gln Thr Arg Leu Asp Phe His Phe Ser Ser Asp Arg Thr Ala Gly Asp
                115                 120                 125
```

| | |
|---|---|
| agg gag gtc cag cag gcc agt ctc atg ttc ttt gtg cag ctc cct tcc<br>Arg Glu Val Gln Gln Ala Ser Leu Met Phe Phe Val Gln Leu Pro Ser<br>            130                    135                    140 | 553 |
| aat acc act tgg acc ttg aaa gtg aga gtc ctt gtg ctg ggt cca cat<br>Asn Thr Thr Trp Thr Leu Lys Val Arg Val Leu Val Leu Gly Pro His<br>        145                    150                    155 | 601 |
| aat acc aac ctc acc ttg gct act cag tac ctg ctg gag gtg gat gcc<br>Asn Thr Asn Leu Thr Leu Ala Thr Gln Tyr Leu Leu Glu Val Asp Ala<br>            160                    165                    170 | 649 |
| agt ggc tgg cat caa ctc ccc cta ggg cct gaa gct caa gct gcc tgc<br>Ser Gly Trp His Gln Leu Pro Leu Gly Pro Glu Ala Gln Ala Ala Cys<br>175                    180                    185                    190 | 697 |
| agc cag ggg cac ctg acc ctg gag ctg gta ctt gaa ggc cag gta gcc<br>Ser Gln Gly His Leu Thr Leu Glu Leu Val Leu Glu Gly Gln Val Ala<br>                195                    200                    205 | 745 |
| cag agc tca gtc atc ctg ggt gga gct gcc cat agg cct ttt gtg gca<br>Gln Ser Ser Val Ile Leu Gly Gly Ala Ala His Arg Pro Phe Val Ala<br>            210                    215                    220 | 793 |
| gcc cgg gtg aga gtt ggg ggc aaa cac cag att cac cga cga ggc atc<br>Ala Arg Val Arg Val Gly Gly Lys His Gln Ile His Arg Arg Gly Ile<br>        225                    230                    235 | 841 |
| gac tgc caa gga ggg tcc agg atg tgc tgt cga caa gag ttt ttt gtg<br>Asp Cys Gln Gly Gly Ser Arg Met Cys Cys Arg Gln Glu Phe Phe Val<br>            240                    245                    250 | 889 |
| gac ttc cgt gag att ggc tgg cac gac tgg atc atc cag cct gag ggc<br>Asp Phe Arg Glu Ile Gly Trp His Asp Trp Ile Ile Gln Pro Glu Gly<br>255                    260                    265                    270 | 937 |
| tac gcc atg aac ttc tgc ata ggg cag tgc cca cta cac ata gca ggc<br>Tyr Ala Met Asn Phe Cys Ile Gly Gln Cys Pro Leu His Ile Ala Gly<br>                275                    280                    285 | 985 |
| atg cct ggt att gct gcc tcc ttt cac act gca gtg ctc aat ctt ctc<br>Met Pro Gly Ile Ala Ala Ser Phe His Thr Ala Val Leu Asn Leu Leu<br>            290                    295                    300 | 1033 |
| aag gcc aac aca gct gca ggc acc act gga ggg ggc tca nnn tgt gta<br>Lys Ala Asn Thr Ala Ala Gly Thr Thr Gly Gly Gly Ser Xaa Cys Val<br>        305                    310                    315 | 1081 |
| ccc acg gcc cgg cgc ccc ctg tct ctg ctc tat tat gac agg gac agc<br>Pro Thr Ala Arg Arg Pro Leu Ser Leu Leu Tyr Tyr Asp Arg Asp Ser<br>            320                    325                    330 | 1129 |
| aac att gtc aag act gac ata cct gac atg gta gta gag gcc tgt ggg<br>Asn Ile Val Lys Thr Asp Ile Pro Asp Met Val Val Glu Ala Cys Gly<br>335                    340                    345                    350 | 1177 |
| tgc agt tagtctatgt gtggtatggg cagcccaagg ttgcatggga aaacacgccc<br>Cys Ser | 1233 |
| ctacagaagt gcacttcctt gagaggaggg aatgacctca ttctctgtcc agaatgtgga | 1293 |
| ctccctcttc ctgagcatct tatggaaatt accccacctt tgacttgaag aaaccttcat | 1353 |
| ctaaagcaag tcactgtgcc atcttcctga ccactaccct cttcctagg gcatagtcca | 1413 |
| tcccgctagt ccatcccgct agccccactc cagggactca gacccatctc caaccatgag | 1473 |
| caatgccatc tggttcccag gcaaagacac ccttagctca cctttaatag accccataac | 1533 |
| ccactatgcc ttcctgtcct ttctactcaa tggtccccac tccaagatga gttgacacaa | 1593 |
| cccctttcccc caattttgt ggatctccag agaggccctt ctttggattc accaaagttt | 1653 |
| agatcactgc tgcccaaaat agaggcttac ctacccccct ctttgttgtg agcccctgtc | 1713 |
| cttcttagtt gtccaggtga actactaaag ctctctttgc ataccttcat ccattttttg | 1773 |
| tccttctctg cctttctcta tgcccttaag gggtgacttg cctgagctct atcacctgag | 1833 |

-continued

```
ctcccctgcc ctctggcttc ctgctgaggt cagggcattt cttatccctg ttccctctct    1893
gtctaggtgt catggttctg tgtaactgtg gctattctgt gtccctacac tacctggcta    1953
cccccttcca tggccccagc tctgcctaca ttctgatttt ttttttttt tttttttga    2013
aaagttaaaa attccttaat ttttattcc tggtaccact accacaattt acagggcaat    2073
atacctgatg taatgaaaag aaaaagaaaa agacaaagct acaacagata aaagacctca    2133
ggaatgtaca tctaattgac actacattgc attaatcaat agctgcactt tttgcaaact    2193
gtggctatga cagtcctgaa caagaagggt ttcctgttta agctgcagta acttttctga    2253
ctatggatca tcgttccctt                                                2272
```

<210> SEQ ID NO 4
<211> LENGTH: 352
<212> TYPE: PRT
<213> ORGANISM: Homo sapiens
<220> FEATURE:
<221> NAME/KEY: misc_feature
<222> LOCATION: (316)..(316)
<223> OTHER INFORMATION: Xaa = any amino acid

<400> SEQUENCE: 4

```
Met Thr Ser Ser Leu Leu Ala Phe Leu Leu Leu Ala Pro Thr Thr
1               5                   10                  15

Val Ala Thr Pro Arg Ala Gly Gly Gln Cys Pro Ala Cys Gly Gly Pro
            20                  25                  30

Thr Leu Glu Leu Glu Ser Gln Arg Glu Leu Leu Leu Asp Leu Ala Lys
        35                  40                  45

Arg Ser Ile Leu Asp Lys Leu His Leu Thr Gln Arg Pro Thr Leu Asn
    50                  55                  60

Arg Pro Val Ser Arg Ala Ala Leu Arg Thr Ala Leu Gln His Leu His
65                  70                  75                  80

Gly Val Pro Gln Gly Ala Leu Leu Glu Asp Asn Arg Glu Gln Glu Cys
                85                  90                  95

Glu Ile Ile Ser Phe Ala Glu Thr Gly Leu Ser Thr Ile Asn Gln Thr
            100                 105                 110

Arg Leu Asp Phe His Phe Ser Ser Asp Arg Thr Ala Gly Asp Arg Glu
        115                 120                 125

Val Gln Gln Ala Ser Leu Met Phe Phe Val Gln Leu Pro Ser Asn Thr
    130                 135                 140

Thr Trp Thr Leu Lys Val Arg Val Leu Val Leu Gly Pro His Asn Thr
145                 150                 155                 160

Asn Leu Thr Leu Ala Thr Gln Tyr Leu Leu Glu Val Asp Ala Ser Gly
                165                 170                 175

Trp His Gln Leu Pro Leu Gly Pro Glu Ala Gln Ala Ala Cys Ser Gln
            180                 185                 190

Gly His Leu Thr Leu Glu Leu Val Leu Glu Gly Gln Val Ala Gln Ser
        195                 200                 205

Ser Val Ile Leu Gly Gly Ala Ala His Arg Pro Phe Val Ala Ala Arg
    210                 215                 220

Val Arg Val Gly Gly Lys His Gln Ile His Arg Arg Gly Ile Asp Cys
225                 230                 235                 240

Gln Gly Gly Ser Arg Met Cys Cys Arg Gln Glu Phe Phe Val Asp Phe
                245                 250                 255

Arg Glu Ile Gly Trp His Asp Trp Ile Ile Gln Pro Glu Gly Tyr Ala
            260                 265                 270
```

```
Met Asn Phe Cys Ile Gly Gln Cys Pro Leu His Ile Ala Gly Met Pro
        275                 280                 285
Gly Ile Ala Ala Ser Phe His Thr Ala Val Leu Asn Leu Leu Lys Ala
        290                 295                 300
Asn Thr Ala Ala Gly Thr Thr Gly Gly Gly Ser Xaa Cys Val Pro Thr
305                 310                 315                 320
Ala Arg Arg Pro Leu Ser Leu Leu Tyr Tyr Asp Arg Asp Ser Asn Ile
            325                 330                 335
Val Lys Thr Asp Ile Pro Asp Met Val Val Glu Ala Cys Gly Cys Ser
            340                 345                 350

<210> SEQ ID NO 5
<211> LENGTH: 30
<212> TYPE: DNA
<213> ORGANISM: Artificial sequence
<220> FEATURE:
<223> OTHER INFORMATION: mutagenic primer directed at human MP52

<400> SEQUENCE: 5
ccacaccacc caccgcctgt gtgcccacgc                                    30

<210> SEQ ID NO 6
<211> LENGTH: 30
<212> TYPE: DNA
<213> ORGANISM: Artificial sequence
<220> FEATURE:
<223> OTHER INFORMATION: mutagenic primer directed at human MP52

<400> SEQUENCE: 6
gcgtgggcac acaggcggtg ggtggtgtgg                                    30

<210> SEQ ID NO 7
<211> LENGTH: 30
<212> TYPE: DNA
<213> ORGANISM: Artificial sequence
<220> FEATURE:
<223> OTHER INFORMATION: mutagenic primer directed at human MP121

<400> SEQUENCE: 7
ctggaggggg ctcagcctgt gtacccacgg                                    30

<210> SEQ ID NO 8
<211> LENGTH: 30
<212> TYPE: DNA
<213> ORGANISM: Artificial sequence
<220> FEATURE:
<223> OTHER INFORMATION: mutagenic primer directed at human MP121

<400> SEQUENCE: 8
ccgtgggtac acaggctgag ccccctccag                                    30

<210> SEQ ID NO 9
<211> LENGTH: 109
<212> TYPE: PRT
<213> ORGANISM: Artificial sequence
<220> FEATURE:
<223> OTHER INFORMATION: consensus sequence of human TGF-beta protein
      superfamily
<220> FEATURE:
<221> NAME/KEY: MISC_FEATURE
<222> LOCATION: (2)..(30)
<223> OTHER INFORMATION: Xaa = any amino acid and this range may
      encompass 25-29 residues
<220> FEATURE:
<221> NAME/KEY: MISC_FEATURE
<222> LOCATION: (32)..(34)
```

```
<223> OTHER INFORMATION: Xaa = any amino acid
<220> FEATURE:
<221> NAME/KEY: MISC_FEATURE
<222> LOCATION: (36)..(70)
<223> OTHER INFORMATION: Xaa = any amino acid and this range may
      encompass 25-35 residues
<220> FEATURE:
<221> NAME/KEY: MISC_FEATURE
<222> LOCATION: (71)..(71)
<223> OTHER INFORMATION: Xaa = any amino acid except cysteine
<220> FEATURE:
<221> NAME/KEY: MISC_FEATURE
<222> LOCATION: (73)..(106)
<223> OTHER INFORMATION: Xaa = any amino acid and this range may
      encompass 27-34 residues
<220> FEATURE:
<221> NAME/KEY: MISC_FEATURE
<222> LOCATION: (108)..(108)
<223> OTHER INFORMATION: Xaa = any amino acid

<400> SEQUENCE: 9

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Cys Xaa
            20                  25                  30

Xaa Xaa Cys Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
            50                  55                  60

Xaa Xaa Xaa Xaa Xaa Xaa Xaa Cys Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Cys Xaa Cys
            100                 105

<210> SEQ ID NO 10
<211> LENGTH: 102
<212> TYPE: PRT
<213> ORGANISM: Artificial sequence
<220> FEATURE:
<223> OTHER INFORMATION: consensus sequence of human TGF-beta protein
      superfamily
<220> FEATURE:
<221> NAME/KEY: MISC_FEATURE
<222> LOCATION: (2)..(29)
<223> OTHER INFORMATION: Xaa = any amino acid
<220> FEATURE:
<221> NAME/KEY: MISC_FEATURE
<222> LOCATION: (31)..(33)
<223> OTHER INFORMATION: Xaa = any amino acid
<220> FEATURE:
<221> NAME/KEY: MISC_FEATURE
<222> LOCATION: (35)..(66)
<223> OTHER INFORMATION: Xaa = any amino acid and this range may
      encompass 30-32 residues
<220> FEATURE:
<221> NAME/KEY: MISC_FEATURE
<222> LOCATION: (67)..(67)
<223> OTHER INFORMATION: Xaa = any amino acid except cysteine
<220> FEATURE:
<221> NAME/KEY: MISC_FEATURE
<222> LOCATION: (69)..(99)
<223> OTHER INFORMATION: Xaa = any amino acid
<220> FEATURE:
<221> NAME/KEY: MISC_FEATURE
<222> LOCATION: (101)..(101)
<223> OTHER INFORMATION: Xaa = any amino acid

<400> SEQUENCE: 10
```

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Cys Xaa Xaa
            20                  25                  30

Xaa Cys Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Cys Xaa Xaa Xaa Xaa Xaa Xaa Xaa Xaa Xaa Xaa Xaa
65              70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Cys Xaa Cys
            100

<210> SEQ ID NO 11
<211> LENGTH: 102
<212> TYPE: PRT
<213> ORGANISM: Artificial sequence
<220> FEATURE:
<223> OTHER INFORMATION: consensus sequence of human TGF-beta protein
      superfamily
<220> FEATURE:
<221> NAME/KEY: MISC_FEATURE
<222> LOCATION: (2)..(29)
<223> OTHER INFORMATION: Xaa = any amino acid except cysteine
<220> FEATURE:
<221> NAME/KEY: MISC_FEATURE
<222> LOCATION: (31)..(33)
<223> OTHER INFORMATION: Xaa = any amino acid except cysteine
<220> FEATURE:
<221> NAME/KEY: MISC_FEATURE
<222> LOCATION: (35)..(67)
<223> OTHER INFORMATION: Xaa = any amino acid except cysteine and this
      range may encompass 31-33 residues
<220> FEATURE:
<221> NAME/KEY: MISC_FEATURE
<222> LOCATION: (69)..(99)
<223> OTHER INFORMATION: Xaa = any amino acid except cysteine
<220> FEATURE:
<221> NAME/KEY: MISC_FEATURE
<222> LOCATION: (101)..(101)
<223> OTHER INFORMATION: Xaa = any amino acid except cysteine

<400> SEQUENCE: 11

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Cys Xaa Xaa
            20                  25                  30

Xaa Cys Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Cys Xaa Xaa Xaa Xaa Xaa Xaa Xaa Xaa Xaa Xaa Xaa
65              70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Cys Xaa Cys
            100

<210> SEQ ID NO 12
<211> LENGTH: 119
<212> TYPE: PRT
<213> ORGANISM: Artificial sequence

```
<220> FEATURE:
<223> OTHER INFORMATION: mutated recombinant human MP52

<400> SEQUENCE: 12

Pro Leu Ala Thr Arg Gln Gly Lys Arg Pro Ser Lys Asn Leu Lys Ala
1               5                   10                  15

Arg Cys Ser Arg Lys Ala Leu His Val Asn Phe Lys Asp Met Gly Trp
            20                  25                  30

Asp Asp Trp Ile Ile Ala Pro Leu Glu Tyr Glu Ala Phe His Cys Glu
        35                  40                  45

Gly Leu Cys Glu Phe Pro Leu Arg Ser His Leu Glu Pro Thr Asn His
    50                  55                  60

Ala Val Ile Gln Thr Leu Met Asn Ser Met Asp Pro Glu Ser Thr Pro
65                  70                  75                  80

Pro Thr Cys Cys Val Pro Thr Arg Leu Ser Pro Ile Ser Ile Leu Phe
                85                  90                  95

Ile Asp Ser Ala Asn Asn Val Val Tyr Lys Gln Tyr Glu Asp Met Val
            100                 105                 110

Val Glu Ser Cys Gly Cys Arg
        115

<210> SEQ ID NO 13
<211> LENGTH: 119
<212> TYPE: PRT
<213> ORGANISM: Artificial sequence
<220> FEATURE:
<223> OTHER INFORMATION: monomeric mutated recombinant human MP52
<220> FEATURE:
<221> NAME/KEY: MISC_FEATURE
<222> LOCATION: (83)..(83)
<223> OTHER INFORMATION: Xaa = any amino acid except cysteine

<400> SEQUENCE: 13

Pro Leu Ala Thr Arg Gln Gly Lys Arg Pro Ser Lys Asn Leu Lys Ala
1               5                   10                  15

Arg Cys Ser Arg Lys Ala Leu His Val Asn Phe Lys Asp Met Gly Trp
            20                  25                  30

Asp Asp Trp Ile Ile Ala Pro Leu Glu Tyr Glu Ala Phe His Cys Glu
        35                  40                  45

Gly Leu Cys Glu Phe Pro Leu Arg Ser His Leu Glu Pro Thr Asn His
    50                  55                  60

Ala Val Ile Gln Thr Leu Met Asn Ser Met Asp Pro Glu Ser Thr Pro
65                  70                  75                  80

Pro Thr Xaa Cys Val Pro Thr Arg Leu Ser Pro Ile Ser Ile Leu Phe
                85                  90                  95

Ile Asp Ser Ala Asn Asn Val Val Tyr Lys Gln Tyr Glu Asp Met Val
            100                 105                 110

Val Glu Ser Cys Gly Cys Arg
        115

<210> SEQ ID NO 14
<211> LENGTH: 101
<212> TYPE: PRT
<213> ORGANISM: Homo sapiens
<220> FEATURE:
<221> NAME/KEY: MISC_FEATURE
<222> LOCATION: (66)..(66)
<223> OTHER INFORMATION: Xaa = any amino acid except cysteine

<400> SEQUENCE: 14
```

-continued

```
Cys Ser Arg Lys Ala Leu His Val Asn Phe Lys Asp Met Gly Trp Asp
1               5                   10                  15

Asp Trp Ile Ile Ala Pro Leu Glu Tyr Glu Ala Phe His Cys Glu Gly
            20                  25                  30

Leu Cys Glu Phe Pro Leu Arg Ser His Leu Glu Pro Thr Asn His Ala
        35                  40                  45

Val Ile Gln Thr Leu Met Asn Ser Met Asp Pro Glu Ser Thr Pro Pro
    50                  55                  60

Thr Xaa Cys Val Pro Thr Arg Leu Ser Pro Ile Ser Ile Leu Phe Ile
65                  70                  75                  80

Asp Ser Ala Asn Asn Val Val Tyr Lys Gln Tyr Glu Asp Met Val Val
                85                  90                  95

Glu Ser Cys Gly Cys
            100
```